United States Patent [19]
Abrioux et al.

[11] Patent Number: 4,494,555
[45] Date of Patent: Jan. 22, 1985

[54] DISCONNECTIBLE APPARATUS COMPRISING A DOUBLE BAYONET COUPLING

[75] Inventors: André H. Abrioux, Drancy; Pierre Corcuff, Neuilly sur Marne; Jean L. Leveque, Le Raincy, all of France

[73] Assignee: L'Oreal, Paris, France

[21] Appl. No.: 474,456

[22] Filed: Mar. 11, 1983

[30] Foreign Application Priority Data

Apr. 8, 1982 [FR] France .............................. 82 06173

[51] Int. Cl.³ ............................................. A61B 10/00
[52] U.S. Cl. .................................... 128/755; 403/348
[58] Field of Search ....................... 128/755, 756, 757; 403/348, 349

[56] References Cited
U.S. PATENT DOCUMENTS

| | | | |
|---|---|---|---|
| 1,171,380 | 2/1916 | Arthur | 403/349 X |
| 2,367,458 | 1/1945 | Coplen | 403/348 |
| 2,592,208 | 4/1952 | Stamper | 403/349 X |
| 2,818,852 | 1/1952 | Kugler | 128/755 |
| 2,820,655 | 1/1958 | Hileman | 403/349 X |
| 3,613,662 | 10/1971 | Chrystomides | 128/755 |
| 3,961,620 | 6/1976 | Schack et al. | 128/757 |
| 4,305,180 | 12/1981 | Schwartz | 403/349 X |

*Primary Examiner*—Edward M. Coven
*Attorney, Agent, or Firm*—Cushman, Darby & Cushman

[57] ABSTRACT

A bayonet drive coupling comprises a barrel and end fitting to be connected by a first bayonet coupling and a spindle and sleeve to be connected by a second bayonet coupling. The second bayonet coupling comprises a slot having a straight entry portion and an oblique second slot portion to receive a pin of the spindle, whereby axial movement of the sleeve is actuated as the pin moves along the second slot portion.

15 Claims, 5 Drawing Figures

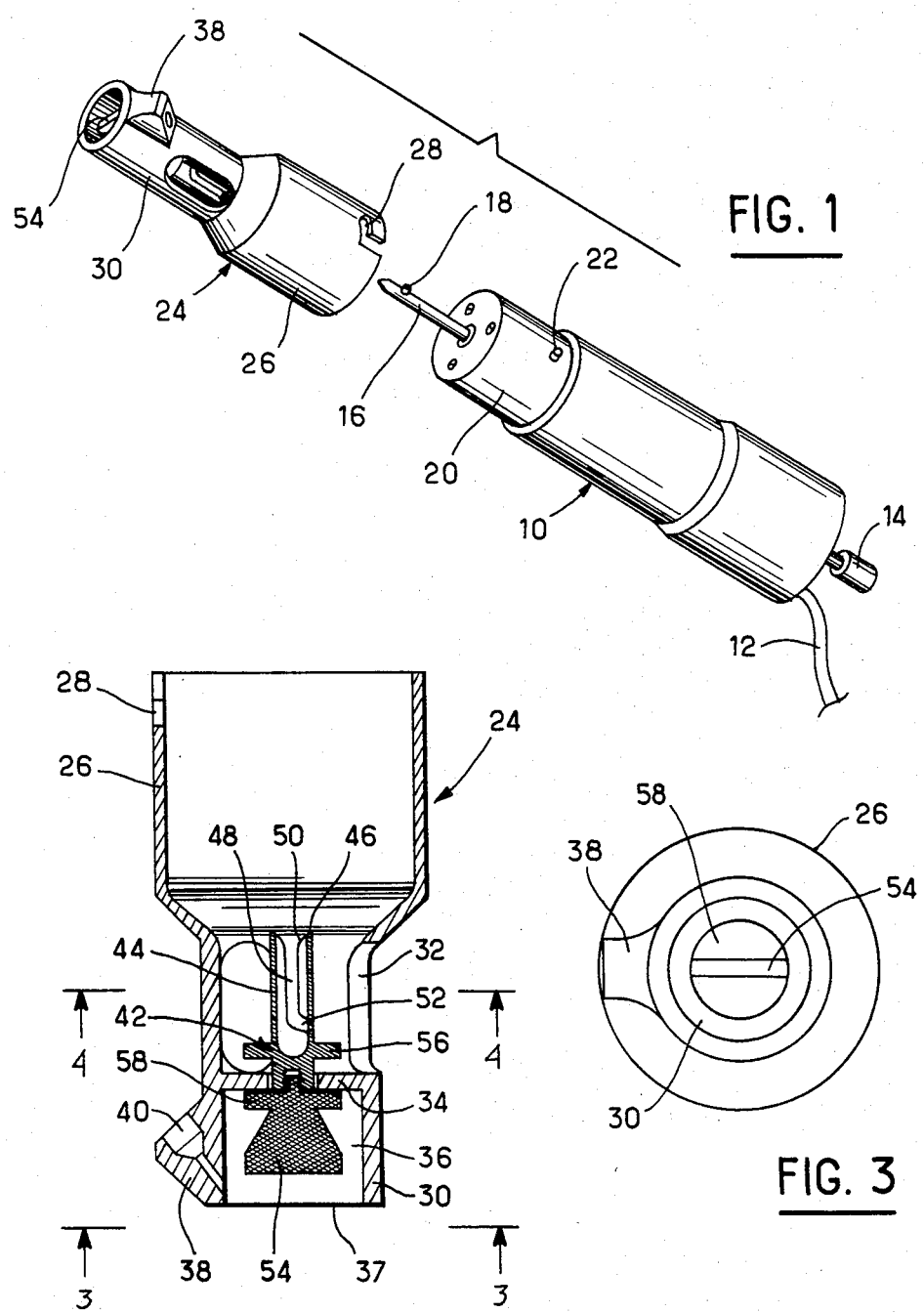

DISCONNECTIBLE APPARATUS COMPRISING A DOUBLE BAYONET COUPLING

The present invention concerns a dismountable apparatus comprising a double bayonet coupling comprising a barrel supporting a rotary unit. For instance the barrel may be the body of a motor having a projecting shaft and an end fitting carrying a rotary tool, such as a blade, the unit and the tool being intended to turn around a common axis of rotation. Such an apparatus is used, for instance, for taking skin cell samples. However, the invention is not restricted to this single application and is suitable for all types of apparatus wherein a rotary tool has to be supported by an end fitting, the tool having to be distinct from the driving motor. For instance, this separation is necessary in the case of the sterilisation of the end fitting and of the rotary tool.

There are already known apparatuses for taking skin cell samples for allowing various physiological properties to be analysed. For instance, knowing the number of cornified cells taken up from the skin, or their nature, makes it possible to diagnose certain diseases.

An apparatus is already known wherein a "turbine-shaped" blade is caused to rotate on contact with the skin. For instance, the article "Measurement of intracorneal cohesion in man using in vivo techniques" by R. Marks, S. Nicholls and D. Fitzgeorge, The Journal of Investigative Dermatology, 69:299–302, 1977, describes such an apparatus for determining the desquamation rate of cornified cells in the cornified epithelial layer. In this apparatus, a rotary blade, placed in contact with the skin, is driven by an electric motor. The force of applying the blade against the skin is constant but may be adjusted. The blade is positioned in a compartment into which a liquid may be introduced.

In accordance with another technique, the rotary blade is not in contact with the skin but the compartment wherein it is rotating contains a surface-active agent. The liquid drawn along by the blade produces the detachment of the cornified cells. The aspiration of the liquid then allows the cornified cells to be counted and analysed.

The above mentioned types of apparatus are intended to be placed in contact with the skin of various patients. They therefore present the risk of contamination if they are not sterilised. However, the sterilisation of apparatus comprising a motor is not simple because only certain techniques can be used. In particular, sterilisation by steam is not possible.

The invention concerns an apparatus comprising a coupling allowing an easy separation of a barrel for instance supporting a motor, and of an end fitting supporting a rotary tool, the end fitting and its tool thus being capable of being sterilised separately from the barrel. This requires a double coupling since it must ensure on the one hand, the connection of the end fitting on the barrel and on the other hand, the connection of the tool to the motor shaft.

More precisely, the invention concerns a disconnectible apparatus comprising a double bayonet coupling between, on the one hand, a barrel and an end fitting, and on the other hand a rotary spindle and a rotor, the spindle being supported by either said barrel or said end fitting and the rotor being supported by the end fitting or the barrel, the spindle and the rotor being intended to turn around the longitudinal axis of the spindle which defines a common axis of rotation, wherein the barrel and the end fitting comprise a first bayonet coupling which can be connected and disconnected by rotation around the said common axis, and the spindle and the rotor comprise a second bayonet coupling which may be connected and disconnected by rotation around said common axis, said spindle being coaxial with the said common axis of rotation and having at least one pin projecting substantially perpendicular to the said common axis; said rotor including a sleeve which is coaxial with said common axis of rotation, and has at least one slot which comprises a first slot part substantially parallel to the common axis of rotation and opening out at an end edge of the sleeve and a second slot portion joined to the first portion and inclined in relation both to said common axis of rotation and to a plane perpendicular to said axis. The barrel may support a rotary assembly, such as a motor, and the end fitting may have its rotor in the form of a rotary tool, the assembly and the tool being intended to turn around the common axis of rotation.

It is advantageous for the slope of the second portion of the slot to be such that the rotational displacement of the pin within this second portion from the first portion of the slot produces an axial entry of the spindle further into the sleeve. In another embodiment, the slope of the second part of the slot is such that this rotational displacement produces a slight axial withdrawal of the spindle relative to the sleeve.

Preferably, the first part of the slot is flared towards an opening ending on the free edge of the sleeve; the plane of the sleeve edge at which the first part of the slot opens out, is oblique in relation to a plane perpendicular to the common axis of rotation, the zone of the end edge into which the opening of the first part of the slot leads being the zone of the edge which is nearest to the second portion of the slot. These two characteristics facilitate the introduction of the pin within the slot during connection of the coupling.

In one embodiment, the end fitting and the tool have devices intended to come to cooperate by way of an axial displacement of the sleeve relative to the spindle, when the pin of the second coupling is displaced towards that end of the second part of the slot which is furthest from the first part of the slot. For instance, the cooperating devices are flanges formed within the end fitting and on the outside of the tool and intended to oppose the flow of a fluid in a direction parallel to the common axis of rotation.

In one embodiment the rotary assembly comprises a motor and the tool comprises a blade, for example a paddle, intended to turn in the end fitting opposite an opening of the end fitting but without projecting therefrom. The end fitting advantageously delimits around such a paddle, a compartment intended to contain a liquid when the opening of the end fitting is closed by contact with the skin of a subject.

In order that the present invention may more readily be understood, a main embodiment, and a variant, shown in the accompanying drawings, will now be described by way of illustrative and non-restrictive examples. In these drawings:

FIG. 1 is an exploded perspective of an apparatus according to the invention for taking cornified cell samples;

FIG. 2 is a longitudinal cross section along the axis of the end fitting of the apparatus of FIG. 1;

FIG. 3 is an end view of the end fitting of FIG. 2, taken along line III—III of FIG. 2;

Figure 4:
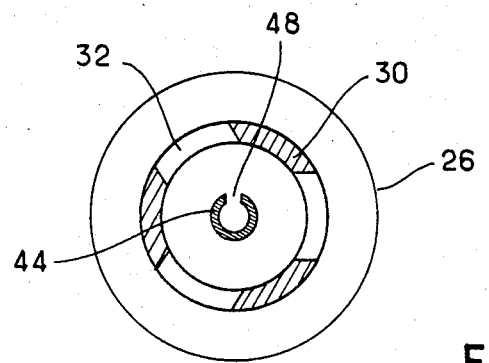
FIG. 4 is a cross section taken along line IV—IV of FIG. 2.

FIG. 1 shows an apparatus as a whole comprising a coupling according to the invention whilst FIGS. 2, 3 and 4 show only the end fitting. The apparatus comprises a barrel 10 housing an electric motor supplied by a lead 12 and controlled by a button 14. The shaft of the motor drives a spindle 16 which carries a radially extending pin 18 near its free end. The spindle 16 is advantageously pointed. This spindle 16 projects from a cylindrical part 20 of the barrel which is provided with two bayonet connector pins 22 which project laterally, that is to say, perpendicular to the axis of rotation of the spindle 16.

The end fitting 24 comprises a first cylindrical portion 26 whose inner diameter is slightly greater than that of the cylindrical part 20 of the barrel 10. The rim of portion 26 nearer the barrel 10 has two L shaped slots 28 to receive the pins 22 for fixing the end fitting 24 on the barrel 10 by rotation, thus forming a known bayonet coupling mechanism.

The end fitting 24 comprises a second cylindrical portion 30 joined to the first via a frustoconical connecting zone. This portion 30 has three openings 32 and it is internally divided into two spaces by a partition 34 which has a central opening. The lower internal part of the cylindrical portion 30 constitutes a chamber 36. This chamber has an opening 37 at the bottom of FIG. 2 giving access to the area of skin to be sampled when this part of the end fitting is applied to the area. Near this lower portion, a projection 38, having a duct 40 ending in chamber 36, allows a liquid to be introduced into this chamber, for instance, by means of a syringe. A tool 42 in the form of a diametrically extending paddle is mounted in the opening of partition 34. This tool 42 has a sleeve 44 ending in an upper edge 46 which has a portion sloping in relation to the axis of the cylindrical portions 26 and 30 so that it opens into a first portion 48 of a slot which has a flared opening 50. The opening 50 constitutes the bottom point of edge 46, that is to say, the point which is nearest to partition 34. This first slot part 48 is extended in a second slot part 52 which is inclined in relation to a plane perpendicular to the axis of the two cylindrical portions 26 and 30.

At its opposite end to the sleeve 44 the tool 42 carries a blade 54. Moreover, two flanges 56 and 58 project laterally from tool 42 on either side of partition 34 and the axial distance separating these two flanges 56 and 58 is greater than the thickness of partition 34. To make assembly possible, the tool 42 is made in two parts which are subsequently assembled, as may duly be seen in FIG. 2.

The end fitting and the tool are preferably both made of metal, for instance of stainless steel, so much so that the unit may be sterilised by steam or in any other way. Barrel 10 may be made of any suitable material, for instance of a moulded plastic material. Spindle 16 is generally made of metal, although this characteristic is not indispensable.

The functioning of the apparatus shown in FIGS. 1 to 4 will now be considered. Before use, the barrel 10 is normally separated from end fitting 24. In effect, the end fitting 24 to be used has been subjected to sterilisation and is therefore kept protected from any contamination. When the taking of the cornified cell samples has to be effected, the end fitting 24 is presented, in the position indicated in FIG. 1, opposite the spindle 16 of barrel 10. The end fitting is then brought towards this spindle along the common axis of rotation of the spindle 16 and tool 42. During this bringing together, the tip of spindle 16 guides the latter inside sleeve 44. When the pin arrives at the level of edge 46, the slope of this edge causes either spindle 16 or tool 42 to rotate until pin 18 becomes aligned on the first part 48 of the slot.

During the continued lowering of end fitting 24, the pin 18 penetrates into the slot and comes as far as the second slot portion 52. At this moment, the cylindrical portion 20 of the barrel has started to penetrate into the cylindrical portion 26 of the end fitting and the user presents the slots 28 opposite the pins 22. The end fitting 24 is then lowered right down against barrel 10 and caused to turn so that the pins 22 engage at the bottom of slots 28. During this rotation, the pin penetrates fully into the second portion 52 of the slot of the tool and/or pushes the latter by rotation.

The apparatus is then ready for use. The operator puts opening 37 into contact with the skin of the subject to be examined. He introduces, via duct 40, a suitable quantity of a liquid, for instance a surfactant liquid. The operator then operates button 14 with the result that the motor causes spindle 16 to rotate at the required speed. The spindle 16 is driven in a direction which causes pin 18 to penetrate as far as the closed end of the inclined second slot portion 52. This is achieved by the pin 18 bearing on the edge of this second inclined portion and performing the function of a cam and it therefore draws tool 42 axially upwardly as viewed in FIG. 2 so that the lower flange 58 comes substantially into contact with the partition 34 of the end fitting. In this way, the liquid contained in the chamber 36 is prevented from escaping via the central opening formed in partition 34.

When the apparatus has been working for a predetermined period, the motor is stopped; the liquid in the chamber 36 is drawn off the duct 40, for instance by use of a syringe, and it may then be examined. The end fitting is simply disconnected by the reverse operations to those that have been described for its assembly. It can then be sterilised again before future use.

An embodiment has been described wherein the second portion 52 of the slot of tool 42 has a slope such that during the rotation of the motor, the tool is drawn upwards in FIG. 2 and therefore ensures the seal by the cooperation of the partition 34 and the flange 58. However, this second slot portion 52 may be sloping in an opposite direction, so that during rotation, the tool will be driven out, i.e. downwardly as viewed in FIG. 2, and the flange 56 then comes substantially into contact with partition 34. The sealing effect obtained is substantially the same, but blade 54 is nearer the skin surface.

Figure 5:
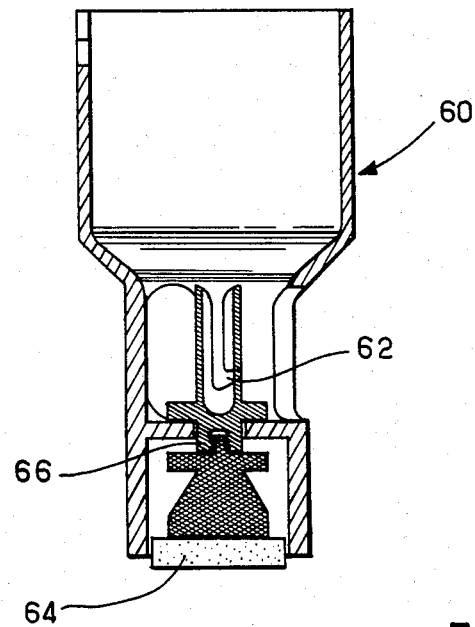
FIG. 5 is an axial longitudinal cross section of a variant of the end fitting in accordance with the invention.

FIG. 5 shows a variant wherein the second slot portion indicated by reference numeral 62, has such a reverse slope. This end fitting 60 has certain differences in relation to the end fitting 24 and it is only these differences which will be described below. The end fitting does not have any projection allowing a liquid to be introduced. Its lower side has a slightly abrasive disc 64 intended to contact the skin. For this purpose, this disc is partially ejected by tool 66. It is therefore necessary for the slope of the second slot portion 62 to be the opposite to that of the corresponding second slot portion 52 of the end fitting of FIG. 2; otherwise, this end fitting is similar to that of FIGS. 1 to 4.

Although we have described the apparatus relating to the application of taking cornified cell samples, the doubling coupling considered has numerous other applications. In particular, it is suitable each time a rotary tool, turning in relation to a stationary end fitting, must be driven to rotate by a motor accommodated in a barrel. This coupling is, above all, advantageous when the slot of the sleeve carried either by the tool or by the drive device terminates in an inclined portion because the tool can then be displaced in one direction or the other along the axis. In one variant, the sleeve 44 may have a double slot having a rising portion to one side of the first slot part and a descending portion to the other side thereof. In this way, depending on the direction of rotation of the spindle 16, the tool is brought axially nearer to or is moved away from the motor.

Although a single slot formed on the sleeve 44 has been described, the latter may comprise several slots. Similarly, the first mentioned coupling of the end fitting 24 on the barrel 10 may comprise any number of pins 22 (i.e. at least one such pin) with a number of slots at least equal to the number of pins.

It shall be duly understood that the coupling described above may give rise to any desirable modification without thereby departing from the scope of the invention as defined by the following claims.

We claim:

1. In a disconnectible apparatus comprising a double bayonet coupling between, on the one hand, a barrel supporting a rotary member, and, on the other hand, an end fitting supporting a rotor, wherein the rotor and the rotary member are intended to rotate, in use, around a common axis of rotation; the improvement wherein:
   (a) the barrel and the end fitting include first bayonet coupling means connectible and disconnectible by relative rotation around said common axis of rotation,
   (b) the rotary member and the rotor include second bayonet coupling means connectible and disconnectible by relative rotation around said common axis of rotation;
   (c) one of said rotary member and said rotor comprising a spindle whose axis is the common axis of rotation, said spindle having at least one pin projecting substantially perpendicular to the said common axis of rotation;
   (d) the other of said rotary member and said rotor comprises a sleeve coaxial with said common axis of rotation, and having a free end edge to receive said spindle; and
   (e) said second bayonet coupling means include said spindle and said sleeve and further include a slot means comprising a first slot portion substantially parallel to said common axis of rotation and opening out at said free end edge of the sleeve, and a second slot portion joined to said first slot portion and inclined in relation to said common axis of rotation and in relation to a plane perpendicular to said common axis of rotation.

2. An apparatus according to claim 1, wherein the slope of the second slot portion is such that the rotational displacement of said pin along said second slot portion away from said first slot portion produces an axial entry of said spindle into said sleeve.

3. An apparatus according to claim 2, wherein the end fitting and the rotor include means intended to come to cooperate by axial displacement of the spindle relative to the sleeve when said pin of the second coupling means is displaced along said second slot portion away from the first slot portion.

4. An apparatus according to claim 3, wherein said means intended to cooperate are a partition of said end fitting and external flanges of said rotor within the fitting, said flanges and partition being adapted to oppose the flow of a fluid in a direction parallel to said common axis of rotation.

5. An apparatus according to claim 1, wherein the slope of the second slot portion is such that the rotational displacement of said pin along said second slot portion away from the first slot portion produces a slight axial disengagement of spindle from said sleeve.

6. An apparatus according to claim 3, wherein the end fitting and the rotor include means intended to come to cooperate by axial displacement of the spindle relative to the sleeve when said pin of the second coupling means is displaced along said second slot portion away from the first slot portion.

7. An apparatus according to claim 6, wherein said means intended to cooperate are a partition of said end fitting and external flanges of said rotor within the end fitting, said flanges and partition being adapted to oppose the flow of fluid in a direction parallel to said common axis of rotation.

8. An apparatus according to claim 1, wherein said first slot portion is flared towards an opening opening out at said free end edge of the sleeve.

9. An apparatus according to claim 8, wherein said free end edge of said sleeve slopes in relation to said plane perpendicular to the common axis of rotation, to define an opening of said first slot portion, the zone of said end edge at which said opening of the first slot portion is arranged being the zone thereof which is nearest to the second slot portion.

10. An apparatus according to claim 1, wherein said spindle is said rotary member and said sleeve is fixed to the rotor.

11. An apparatus according to claim 1, wherein said end fitting has an end opening, wherein the rotary assembly comprises a motor having said spindle as its driven member, and wherein said rotor comprises a blade arranged to turn in the end fitting opposite said end opening thereof without projecting outwardly of said end fitting.

12. An apparatus according to claim 11, wherein said end fitting defines around said blade chamber means intended to contain a liquid when said opening of the end fitting is closed by contact with the skin of a subject whose skin cells are to be sampled.

13. In a disconnectible apparatus comprising a double bayonet coupling between, on the one hand, a barrel supporting a motor and, on the other hand, an end fitting supporting a rotor, said rotor and motor being intended to rotate in use around a common axis of rotation, and said motor having a driven spindle adapted to drivingly rotate said rotor; the improvement wherein:
   (a) the barrel and the end fitting include first bayonet coupling means connectible and disconnectible by relative rotation around said common axis of rotation;
   (b) the spindle and the rotor include second bayonet coupling means connectible and disconnectible by relative rotation around said common axis of rotation;
   (c) said spindle includes pin means projecting substantially perpendicular to said common axis of rotation;

(d) said rotor comprises a sleeve coaxial with said common axis of rotation and having a free end edge adjacent said barrel;

(e) said second bayonet coupling means include said spindle and said sleeve and further include slot means comprising a first slot portion substantially parallel to said common axis of rotation and opening out at said free end edge of the sleeve, and a second slot portion joined to said first slot portion and inclined in relation to said common axis of rotation and in relation to a plane perpendicular to said common axis of rotation;

(f) said end fitting includes a means defining an open end thereof, first chamber means adapted to receive said spindle, second chamber means adapted to receive a liquid when said end opening of the end fitting is closed by contact with the skin of the subject whose skin cells are to be sampled, and a partition separating said first and second chamber means;

(g) said rotor includes first and second external flanges positioned within said end fitting; and (h) said second bayonet coupling means includes means effecting relative axial movement of said rotor within said end fitting in response to drive torque between said spindle and said rotor.

14. An apparatus according to claim 13, wherein said means for effecting axial displacement of said rotor comprise side walls of said second slot portion cammingly engaging said pin means such that driving rotation of said rotor by means of said spindle effects movement of said rotor towards said end opening of said end fitting.

15. An apparatus according to claim 13, wherein said means for effecting axial displacement of said rotor comprise side walls of a second slot portion cammingly engaging said pin means so as to effect withdrawal of said rotor away from said end opening of the end fitting in response to drive torque exerted on said rotor by means of said spindle.

* * * * *